United States Patent [19]

Moore

[11] Patent Number: 4,901,355
[45] Date of Patent: Feb. 13, 1990

[54] COMBINATION MULTIPLE SUPPORTED VARIABLE POSITION AUDIO INTAKE CONTROL DEVICES

[76] Inventor: Michael R. Moore, P.O. Box 1761, La Jolla, Calif. 92038

[21] Appl. No.: 134,613

[22] Filed: Dec. 14, 1987

Related U.S. Application Data

[63] Continuation of Ser. No. 892,641, Aug. 4, 1986, abandoned.

[51] Int. Cl.⁴ .......................... H04M 1/05; H04R 1/10
[52] U.S. Cl. .................................... 381/183; 381/68.5; 381/187
[58] Field of Search ................ 381/183, 187, 68.5; 379/430

[56] References Cited

U.S. PATENT DOCUMENTS

| | | | |
|---|---|---|---|
| 1,714,377 | 5/1929 | Kiernan | 381/183 |
| 2,337,953 | 12/1943 | Wirsching | 381/183 |
| 2,424,935 | 7/1947 | Kimmel | 381/68.5 |
| 2,501,107 | 3/1950 | Volkmann | 381/183 |
| 2,573,132 | 10/1951 | French | 381/187 |
| 2,641,327 | 6/1953 | Balmer | 381/187 |
| 2,874,230 | 2/1959 | Carlson | 381/68.5 |
| 3,588,384 | 6/1971 | Negley | 381/68.5 |
| 3,667,569 | 6/1972 | Mackey et al. | 381/187 |
| 3,871,372 | 3/1975 | Bivins | 381/685 |
| 4,189,788 | 2/1980 | Schenke et al. | 381/183 |
| 4,420,657 | 12/1983 | Larkin | 379/430 |
| 4,485,276 | 11/1984 | Sato | 381/183 |
| 4,499,593 | 2/1985 | Antle | 381/183 |
| 4,538,034 | 8/1985 | French | 381/187 |
| 4,542,803 | 9/1985 | Houng | 381/183 |

FOREIGN PATENT DOCUMENTS

| | | | |
|---|---|---|---|
| 273259 | 8/1969 | Austria | 381/68.5 |
| 2351504 | 4/1975 | Fed. Rep. of Germany | 381/187 |
| 2289090 | 5/1976 | France | 381/68.5 |
| 61-95696 | 5/1986 | Japan | 381/183 |
| 1144294 | 3/1969 | United Kingdom | 381/187 |

*Primary Examiner*—Jin F. Ng
*Assistant Examiner*—Danita R. Byrd

[57] ABSTRACT

A personal audio assembly including a pair of miniature speakers releasably connected with the sidepieces of a pair of spectacles or headgear in a manner permitting adjustment of the speakers longitudinally, angularly and vertically with respect to the sidepieces or headgear and toward and away from the ears of a user. Leads connect the speakers with an audio source controlling sound entering the ear and are provided with an adjusting member maintaining the speakers in a selected.

13 Claims, 2 Drawing Sheets

COMBINATION MULTIPLE SUPPORTED VARIABLE POSITION AUDIO INTAKE CONTROL DEVICES

This application is a continuation of application Ser. No. 892,641, filed Aug. 4, 1986, now abandoned.

BACKGROUND OF THE INVENTION

1. Field of the invention.

The present invention relates to audio communication and more particularly to a sound intake control device and adjustable supports therefor.

Radios, tape players and other audio equipment have been miniaturized to such an extent that they may be conveniently carried on the person of a user, such as in a pocket or other portion of the wearer's clothing or accessories. Many diverse audio sources are now in use.

A need in terms of safety, further choice in listening capability, and the intake and/or blocking of external sounds has arisen. This device has been created to answer the needs of pilots, communications personnel, music lovers, airport linemen or anyone with the need to hear more than one audio source simultaneously and/or in regulated quantities or levels. This invention is designed to accurately achieve multiple source sound (sound on sound), single source sound or no sound.

Presently and as technological and social change occur the demand for safety, utility and convenience are major considerations. A device which provides a means for greater discrimination of aural sources will aid many people who desire to listen, communicate and deal with sound more effectively.

This invention is also directed toward a means of providing high quality sound reproduction with the versatility to be utilized as a headset, earphones and/or hearing aid or earplugs. The device can be worn in combination with, or as a means to secure spectacles or headgear of the wearer. The design places the device where it can be utilized on a regular basis.

This invention is directed toward a manner of mounting miniature speakers or earphones to enhance their utility, versatility and minimize any inconvenience or discomfort as a result of the supporting components.

2. Description of the prior art.

At present audio headsets and earphones are limited to a single position; existing headsets and earphones enclose the ear, are pressed adjacent to the ear, are placed in the outer ear, or, are positioned inside the auditory canal.

Prior art, due to this single position limitation, has the inherent effect of masking outside sounds with sound produced by the earphones. With respect to safety, the wearer is hindered in his ability to hear surrounding sounds such as instructions, warnings, automobiles, sirens, conversations etc.

The most widely used, present design audio headset is awkward to wear and cumbersome to carry. Cord entanglement problems occur regularly and the resulting entanglement can cause short circuiting of speaker or microphone leads, as well as incur the bother and loss of time spent untangling headset wires.

Additional entanglement problems arise when the now common "leash" (a retainer cord used to suspend the glasses around the wearer's neck when not in use) is worn simultaneously with the prior art headset.

Another difficulty involves the wearing of a hat, visor or helmet and a prior art headset simultaneously. Since the majority of headsets in use today consist of a band, which transversely spans the head, a hat, helmet or visor does not fit the wearer's head properly when worn in combination with the headset. At present the small in ear-type headsets circumvent this problem however sound quality is sacrificed due to the extra small size of the speakers and they are limited to a single position.

Further shortcomings of prior art include the lack of single hand placement. Both hands are needed to place the headset or earphones in listening position.

Other prior art devices disclose speakers or earphones used as hearing aids for the hard of hearing some of which were supported by spectacles or constructed as a part thereof, such as disclosed by Pat. No. 2,874,230 in which the terminal end of the respective sidepiece supports a speaker.

The present invention is distinctive over prior art devices by adjustably supporting a pair of miniature speakers on headgear or spectacle sidepieces which can be positioned in the ear, adjacent the ear or in varying distances from the ear as desired. The inherent design serves multiple functions and places the sound in the control device where it can be safely heard, worn, transported and utilized more effectively.

SUMMARY OF THE INVENTION

A pair of miniature speakers, each connected with one end of an audio lead are provided with members connecting the respective speaker to means on the head of the user, such as a respective spectacle sidepiece or headgear having a band horizontally surrounding the head of the user or the user's hair which supports each speaker in depending relation for vertical adjustment of the speaker toward and away from the sidepiece or headgear and for horizontal movement longitudinally of the sidepiece or headgear. The other end of the respective audio lead is joined to a plug removably received by an audio jack in equipment supplying an audio signal. An audio lead gripping member surrounds the two leads intermediate their ends which serves to maintain the two leads in single cord fashion and by sliding movement longitudinally of the leads acts as a retainer or chin strap for maintaining the speakers and the glasses sidpiece adjacent the user's ears when the leads are located in front of the user's neck, or alternatively as a support or leash for hanging the speakers and spectacles from the user's neck when the leads and plug end extend rearwardly of the user's neck.

Horizontal movement of the speakers longitudinally of the sidepieces or headgear allows the user to position the speakers relative to the ear as desired. If very little external sound is desired to be heard, the user locates the speakers in or adjacent the ears. If more external sound is desired, the speakers are moved forwardly and away from the ears as necessary and the volume adjusted to attain the desired ratio of speaker and external sound mixing (sound on sound).

Vertical movement of the speakers relative to the glasses allows accurate positioning with respect to the ear for different individuals and different sidepieces. Additionally, the vertical movement can be utilized to perform the external sound versus speaker sound (sound on sound) adjustment as primarily achieved by the horizontal positioning.

The attachment to the spectacles or headgear allows the device to be placed near the ears safely and easily with only one hand because the spectacles or headgear are designed for single hand placement. This eliminates the cord entanglement aggravation caused when combining a headset with a spectacle leash, by combining both devices into one apparatus.

The principal objects of this invention are to provide a personal user supported audio unit comprising a relatively inexpensive assembly of audio earphones easily connected with and supported by headgear or the sidepieces of any conventional pair of spectacles and which may be adjusted relative to the headgear or sidepiece either laterally longitudinally or vertically to position the ear-phones in a comfortable position adjacent or within the ear for maximum audio and which can enable the user to hear and identify sounds from sources other than the audio set connected with the earphones.

DESCRIPTION OF THE PREFERRED EMBODIMENTS

Figure 1:
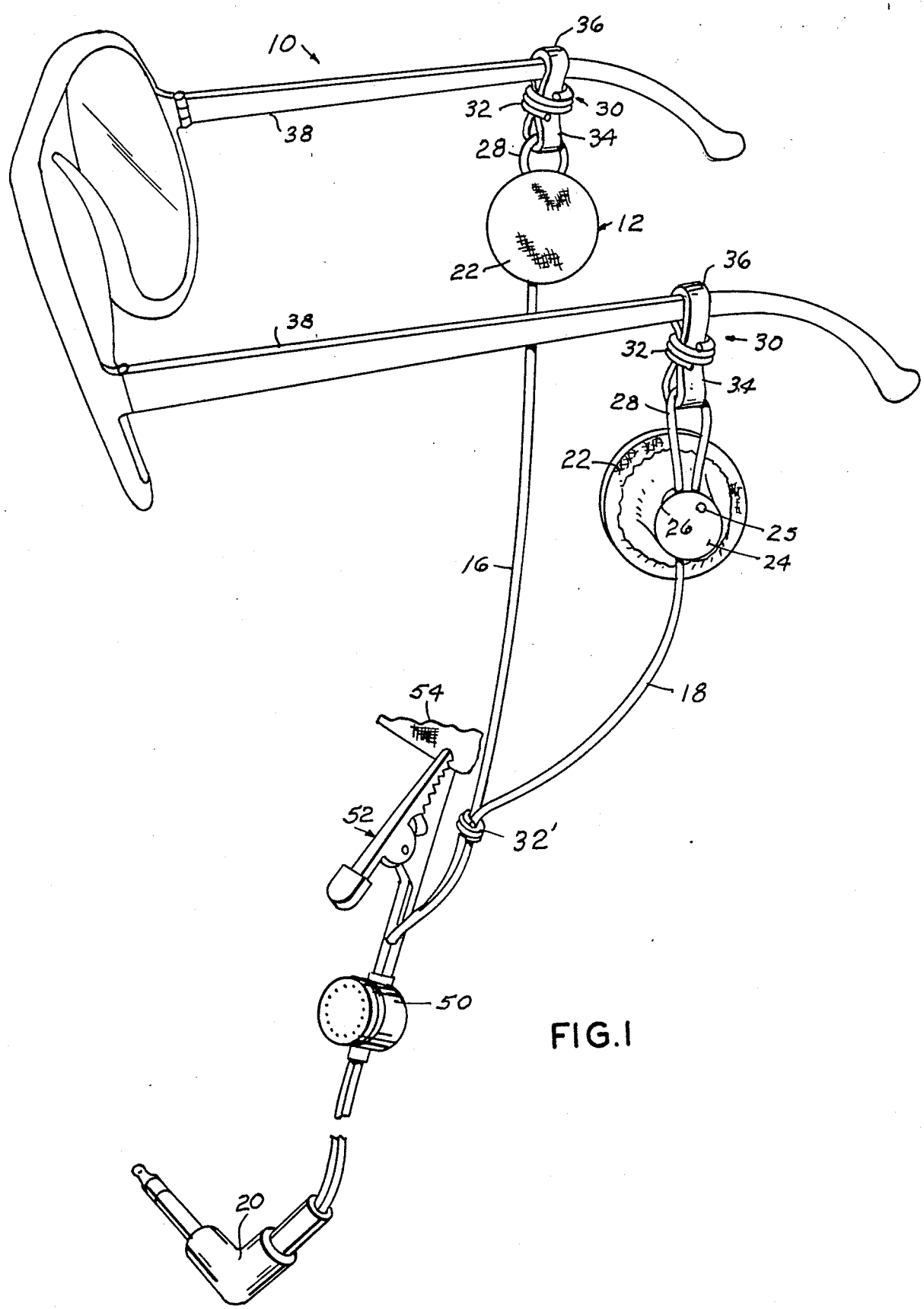
FIG. 1 is a perspective view of the device supported by a pair of spectacles.

Like characters of reference designate like parts in those figures of the drawings in which they occur.

In the drawings:

The reference numeral 10 indicates the unit as a whole. The device 10 comprises a pair of conventional, commercially available miniature speakers 12 and 14 operatively connected with one end of audio leads 16 and 18, respectively, with the other end of the leads connected with a plug 20 in a conventional manner. Each of the speakers may include a cover 22 through which audio sounds are transmitted and an opposite or rearward substantially cylindrical portion 24, having a vent 25, which receives and is connected with the above named one end portion of the respective audio lead. The respective cylindrical portion 24 is transversely apertured, as at 26, for frictionally receiving, in sliding relation, a portion of the respective audio lead adjacent its connected end to form an audio lead closed loop portion 28 which may be increased or reduced in size to allow the speakers 12 or 14 to be moved vertically for adjustment purposes.

A flexible connector 30 is connected with each speaker loop 28. The flexible connectors 30 are preferably endless bands with juxtaposed portions of its wall surrounded and gripped in sliding relation by a tension adjuster 32 to define a substantially figure eight configuration.

The connectors 30 may be formed by an endless band or may be a strap-like length of flexible plastic material doubled back upon itself from both of its ends and secured together. A tension adjuster 32, transversely surrounding the connector band, is formed by a helically twisted length of wire, or the like, and defines oppositely disposed closed loops 34 and 36 at respective ends of the flexible connector. The loop 34 is engaged with the speaker loop 28 in chain link fashion and the other loop 36 of the flexible connector transversely surrounds a respective one of a pair of spectacle sidepieces 38 intermediate its ends. The loop 36 allows horizontal movement of the speakers longitudinally of the respective sidepiece.

A tension adjuster member 32' also surrounds the audio leads 16 and 18 intermediate their ends for the purpose presently explained. A rheostat 50 is interposed in the leads 16 and 18 between the tension adjuster 32' and the plug 20 as a volume control. An alligator-type clip or clamp 52 is attached to the leads between the volume control 50 and the tension adjuster 32' for supporting the volume control in a convenient location as by attaching the clamp 52 to a portion of the user's clothing 54.

Figure 2:
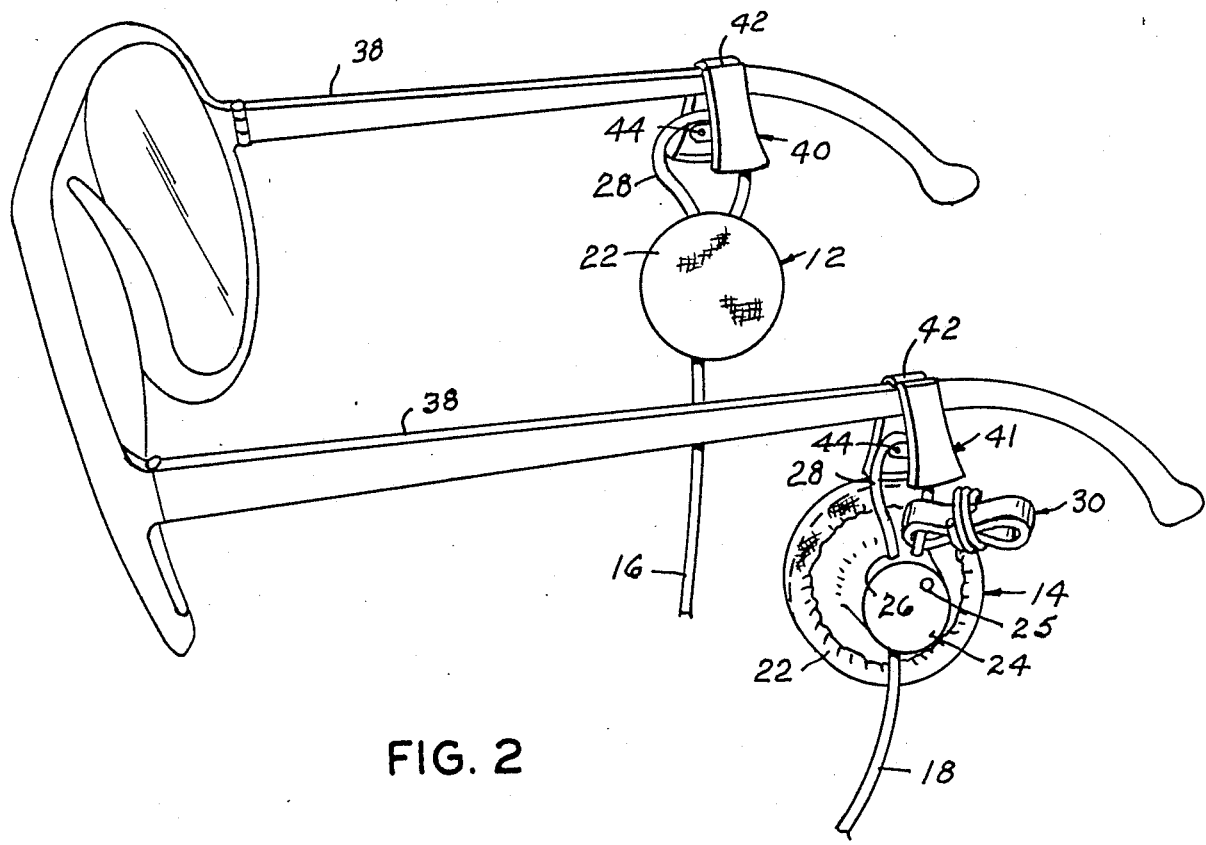
FIG. 2 is a fragmentary view similar to FIG. 1 illustrating spring clips supporting the device on the spectacle sidepiece.
Figure 3:
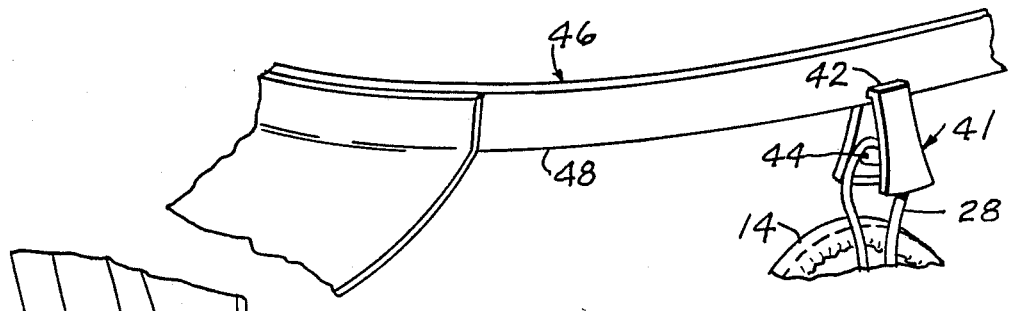
FIG. 3 is a fragmentary perspective view illustrating the manner of supporting the device on the user's visor or other head encircling band; and, FIG. 4 is a fragmentary perspective, similar to FIG. 2, illustrating another embodiment.

Referring also to FIGS. 2 and 3, the reference numerals 40 and 41 indicate a pair of spring clips or clamps which may be used in place of the connectors 30. This is accomplished by permanent attachment of the clamp to the speaker cord or manually opening the respective spring clamp so that the speaker cord loop 28 is received between the gripping end portion 42 of the clamp and its spring closed hinged connection 44 so that the respective speaker 12 or 14 is then supported in depending relation from the respective clamp. The clamp gripping end 42 is then disposed on opposing sides of the respective spectacle sidepiece 38 at a selected location intermediate its length.

In the event the user of the device does not wear spectacles, the clamps 40 permit attachment to other headgear, such as the sweatband of a hat, not shown, or the band of a visor, as indicated at 46 (FIG. 3). The respective clamp 40 and 41 is positioned as shown with its gripping end edge 42 gripping opposing sides of the depending edge portion of the visor band 48.

Figure 4:
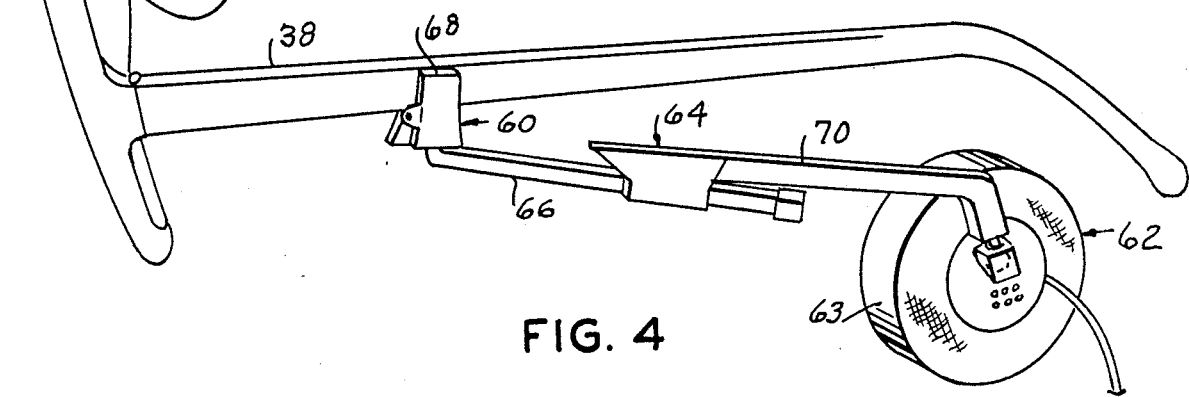

Referring more particularly to FIG. 4 other clamps 60, only one being shown, similarly gripping the spectacle earpieces 38, support similar speakers 62 in cantilever fashion by arm means 64. A pad 63 surrounds the major portion of the speaker. In the example shown the arm means 64 comprises a forward bar 66 rigidly attached at one end to the clamp 60 opposite its gripping end portion 68 and longitudinally slidably attached at its other end portion to the forward end portion of a rearward arm 70 having its opposite or rearward end rigidly secured to the speaker 62. This permits vertical adjustment of the speaker relative to the sidepiece 38 and the user's ear, not shown, by the angular position of the clamp 60 relative to the longitudinal axis of the sidepiece. Forward and rearward adjustment of the speaker 62 relative to the sidepiece and the user's ear is achieved primarily by the sliding movement of the arm 70 relative to the bar 66 and secondly by the position of the clamp 60 longitudinally of the sidepiece. It seems obvious that the arm 70 may serve as a gooseneck having a ball at its rearward end cooperatively received by a socket formed in the housing supporting the speaker components to impart substantially all the advantages of ball and socket movement of the speaker 62 relative to the user's ear, if desired.

OPERATION

In use the flexible connectors 30 have their free loop ends 36 transversely surrounding the respective spectacle sidepiece. With the spectacles in wearing position, the speakers are adjusted by moving the flexible connectors 30 longitudinally of the respective sidepiece so that the speakers are positioned relative to the user's ear in a desired position in accordance with other parameters which may or may not be limiting the user's attention. For example, the speakers may be positioned so that a desired audio program may be heard and yet other sounds may also be received, such as automobiles, warnings, instructions or the conversations of others. By moving the adjuster 32 toward the respective sidepiece the size of the loop 36 is reduced to grip the sidepiece so the speakers are frictionally maintained adjacent or in the user's audio canal, as desired. The speakers may be positioned independently of each other to further enhance listening capabilities.

The strap-like configuration of the connectors 30, in combination with a small size for the loop 34, prevents angular rotation of either speaker about a vertical axis through the respective connector 30. The coefficient of sliding friction between the connector loop 36 and the surface of the sidepiece 38 prevents movement of one component relative to the other except as manually induced. The speakers are easily adjusted vertically relative to the sidepieces or the user's ears by increasing or decreasing the size of the lead loop 28. Further, if the user desires the speakers to be in close proximity to the ear the lead adjuster 32' may be moved longitudinally of the leads until disposed in underlying relation with respect to the user's chin to place a slight tension on the leads 16 and 18 and draw the speakers inwardly toward each other.

Alternatively, the leads may be positioned rearwardly of the user's head and the adjuster 32' disposed adjacent the back of the head to maintain the speakers adjacent the ears and to maintain the spectacles in place on the face of the user. In this position the speaker assembly 10 may also be employed to support the spectacles in a position hanging from the user's neck.

It seems obvious that the spring clamps 40 and 41 may be connected with the lead loops 28, as described hereinabove, for use with the headgear as desired.

Obviously the invention is susceptible to changes or alterations without defeating its practicability. Therefore, I do not wish to be confined to the preferred embodiment shown in the drawings and described herein.

I claim:

1. A personal audio unit for connection with an audio source, comprising:
    a pair of speakers;
    flexible leads extending between and having opposing ends respectively operatively connecting said speakers with an audio source;
    mounting means including a clamp secured to each speaker of said pair of speakers for attachment with means on the head of a user, wherein the mounting means adjustably supports the respective speaker of said pair of speakers in variable positions enabling the user to select and hear combined sounds, the combined sounds including speaker generated sounds mixed with external, ambient sounds;
    each speaker of said pair of speakers having a cylindrical portion and having a transverse aperture therethrough slidably receiving an intermediate portion of the respective lead for forming a closed leading loop adjacent the speaker connected end of the respective lead; and,
    said clamp surrounding an intermediate portion of the respective lead forming the lead loop in speaker supporting relation.

2. The audio unit according to claim 1 in which the means on the head of the user includes:
    a pair of spectacles having sidepieces adapted for engaging a user's head adjacent the ears for supporting the spectacles; and wherein
    each mounting means adjustably connects each speaker of said pair of speakers with the respective sidepiece of said spectacles for manual longitudinal adjustment along an intermediate portion of the respective sidepiece, each mounting means also being connected, in chain link fashion, with the respective closed lead loop for permitting swinging movement of the respective speaker toward and away from a user's head.

3. The combination according to claim 1 in which each flexible connector comprises:
    an endless strap-like band; and,
    a first tension means including a helically wound strand transversely surrounding, in frictional sliding relation, juxtaposed intermediate portions of the respective band for reducing the area encompassed by the sidepiece surrounding closed connector loop and precluding movement of the respective flexible connector relative to the attached sidepiece.

4. The combination according to claim 3 in which the other end portion of the flexible leads depend from the speakers and further including:
    a second tension means frictionally slidably surrounding the flexible leads intermediate their ends for limiting movement of the pair of speakers away from a user's head when the spectacles are in normal wearing position and the second tension means is disposed toward the speaker connected end of the leads.

5. A personal audio unit as claimed in claim 1, wherein the speakers are positioned within the user's ears, thereby preventing a substantial amount of the external, ambient sounds from being heard by the user.

6. A personal audio unit as claimed in claim 1, wherein the speakers are positioned forwardly and away from the user's ears, thereby allowing the user to clearly and simultaneously hear sounds coming from the speakers as well as the sounds coming from external, ambient sources.

7. A personal audio unit for connection with an audio source, comprising:
    a pair of speakers;
    flexible leads extending between and having opposing ends respectively operatively connecting said speakers with an audio source;
    mounting means including a clamp secured to each speaker of said pair of speakers for attachment with means on the head of a user, wherein the mounting means adjustably supports the respective speaker of said pair of speakers in variable positions enabling the user to select and hear combined sounds, the combined sounds including speaker generated sounds mixed with external, ambient sounds;
    a pair of spectacles having sidepieces adjacent and extending forwardly from the ears of the user; and,
    a pair of elongated arm means slidably connected together at one end portion in longitudinal overlapping relation and connected at their other ends with the respective said clamp and speaker of said pair of speakers.

8. A personal audio unit for connection with an audio source, comprising:
    a pair of speakers;

flexible lead extending between and having opposing ends respectively operatively connecting said speakers with an audio source;

mounting means including a clamp secured to each speaker of said pair of speakers for attachment with means on the head of a user and supporting the respective speaker of said pair of speakers in a predetermined audio range position relative to the user's ears; and wherein each speaker of said pair of speakers having a cylindrical portion and having a transverse aperture therethrough slidably receiving an intermediate portion of the respective lead for forming a closed lead loop adjacent the speaker connected end of the respective lead; and, said clamp surrounding an intermediate portion of the respective lead forming the lead loop in speaker supporting relation.

9. A personal audio unit for connection with an audio source, comprising:

a pair of speakers;

flexible leads extending between and having opposing ends respectively operatively connecting said speakers with an audio source; and, mounting means including a clamp for attachment with means on the head of a user and supporting the respective speaker of said pair of speakers in a desired position relative to the user's ears, said mounting means further including: a pair of spectacles having sidepieces adapted for engaging a user's head adjacent the ears for supporting the spectacles, each speaker of said pair of speakers having a cylindrical portion and having a transverse aperture therethrough slidably receiving an intermediate portion of the respective lead for forming a closed lead loop adjacent the speaker connected end of the respective lead; and, means adjustably connecting each speaker of said pair of speakers with the respective sidepiece of said spectacles including an elongated flexible connector having a closed connector loop at each of its ends respectively surrounding for manual adjustment longitudinally along an intermediate portion of an sidepiece and connected, in chain link fashion, with a respective said closed lead loop for permitting swinging movement of each speaker of said pair of speakers toward and away from a user's head and disposing each speaker of said pair of speakers in a predetermined position relative to the user's ears.

10. The audio unit according to claim 9 in which each flexible connector comprises:

an endless strap-like band; and, a first tension means including a helically wound strand transversely surrounding, in frictional sliding relation, juxtaposed intermediate portions of the respective band or reducing the area encompassed by the sidepiece surrounding closed connector loop and precluding movement of the respective flexible connector relative to the attached sidepiece.

11. The audio unit according to claim 10 in which the other end portion of the flexible leads depend from the speakers and further including:

a second tension means frictionally slidably surrounding the flexible leads intermediate their ends for limiting movement of the pair of speakers away from a user's head when the spectacles are in normal wearing position and the second tension means is disposed toward the speaker connected end of the leads.

12. A personal audio unit for connection with an audio source, comprising:

a pair of speakers;

flexible leads extending between and having opposing ends respectively operatively connecting said speakers with an audio source;

mounting means including a clamp secured to each speaker of said pair of speakers for attachment with means on the head of a user and supporting the respective speaker of said pair of speakers in a desired position relative to the user's ears;

a pair of elongated arm means slidably connected together at one end portion in longitudinal overlapping relation and connected at their other ends with the respective said clamp and speaker of said pair of speakers.

13. A personal audio unit for connection with an audio source, comprising:

a pair of speakers;

flexible leads extending between and having opposing ends respectively operatively connecting said speakers with an audio source; and, mounting means including a clamp secured to each speaker of said pair of speakers for attachment with means on the head of a user and supporting the respective speaker of said pair of speakers in a desired position relative to the user's ears, said means on the head of the user further including: a pair of spectacles having sidepieces adjacent and extending forwardly from the ears of the user; and, a pair of elongated arm means slidably connected together at one end portion in longitudinal overlapping relation and connected at their other ends with the respective said clamp and speaker of said pair of speakers.

* * * * *

UNITED STATES PATENT OFFICE
CERTIFICATE OF CORRECTION

PATENT NO. : 4,901,355
DATED : Feb. 13, 1990
INVENTOR(S) : Michael R. Moore

It is certified that error appears in the above-identified patent and that said Letters Patent is hereby corrected as shown below:

On the title page:

In the Abstract, the following should be added before the period in the last line --position allowing the user to simultaneously hear a combination of speaker and ambient sounds--.

Signed and Sealed this

Nineteenth Day of February, 1991

Attest:

HARRY F. MANBECK, JR.

*Attesting Officer*      *Commissioner of Patents and Trademarks*